United States Patent
Pazouki

(10) Patent No.: US 9,700,488 B1
(45) Date of Patent: Jul. 11, 2017

(54) VIAL AND STYLET HOLDER FOR A MEDICAL PROCEDURE

(71) Applicant: Narges Pazouki, Turlock, CA (US)

(72) Inventor: Narges Pazouki, Turlock, CA (US)

( * ) Notice: Subject to any disclaimer, the term of this patent is extended or adjusted under 35 U.S.C. 154(b) by 0 days.

(21) Appl. No.: 15/137,876

(22) Filed: Apr. 25, 2016

Related U.S. Application Data

(63) Continuation-in-part of application No. 14/500,965, filed on Sep. 29, 2014.

(51) Int. Cl.
*A45F 5/00* (2006.01)
*A61J 1/16* (2006.01)
*A61B 10/00* (2006.01)

(52) U.S. Cl.
CPC .............. *A61J 1/16* (2013.01); *A61B 10/0045* (2013.01); *A61B 2010/0077* (2013.01)

(58) Field of Classification Search
CPC ..... B25H 3/04; A47F 7/0028; A47G 25/0657; A47G 23/0241; A47G 29/08; A45F 5/10; F16L 3/13; F16L 3/2235; B60R 1/076; B65D 85/20; B65D 25/108; B65D 25/54; A61B 19/0271; A61B 10/0045; A61B 2010/0077; A61C 19/02; A61J 1/16
USPC .......................................................... 206/370
See application file for complete search history.

(56) References Cited

U.S. PATENT DOCUMENTS

| | | | | |
|---|---|---|---|---|
| 1,980,930 A * | 11/1934 | Reyniers | .................. | B01L 9/06 211/74 |
| 4,510,119 A * | 4/1985 | Hevey | ................. | B01L 3/50853 206/443 |
| 5,615,782 A * | 4/1997 | Choe | ........................ | A45D 1/00 211/60.1 |
| 7,565,979 B1 * | 7/2009 | Gibson | ..................... | A61J 7/04 206/363 |
| 2011/0186456 A1 * | 8/2011 | Bertazzoni | ............. | A61B 50/33 206/438 |
| 2014/0021079 A1 * | 1/2014 | Koller | .................. | A47F 7/0028 206/370 |

* cited by examiner

*Primary Examiner* — Stephen Vu
(74) *Attorney, Agent, or Firm* — Law Office of Rodney LeRoy

(57) ABSTRACT

A vial and stylet holder includes a frame, a handle, and vial holders coupled to the frame. Each vial holders includes a tube that is adapted to receive and hold a vial. The vial and stylet holder includes a stylet receptacle coupled to the frame. The stylet receptacle includes a tube having an opening at a first end and a longitudinal axis of the tube is parallel to longitudinal axes of each of the tubes of the vial holders. The stylet receptacle is adapted to hold a stylet of a puncture needle.

19 Claims, 20 Drawing Sheets

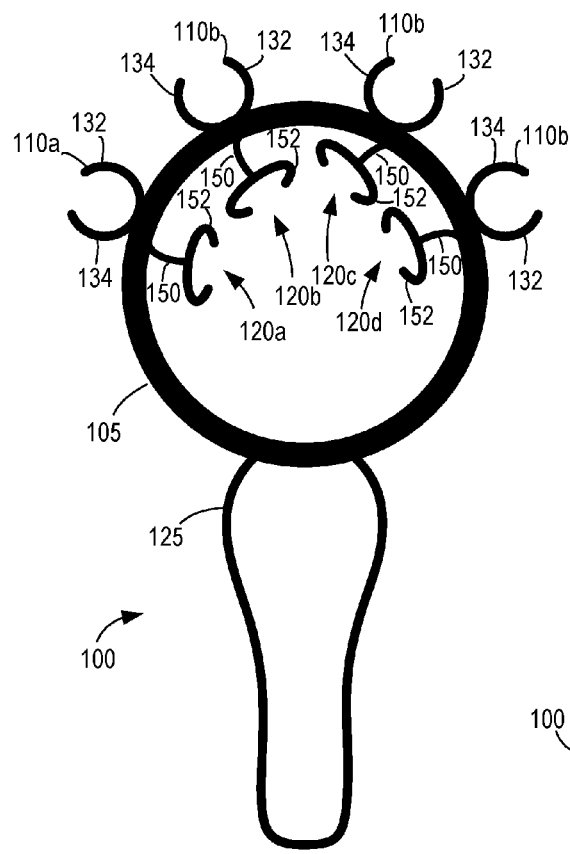
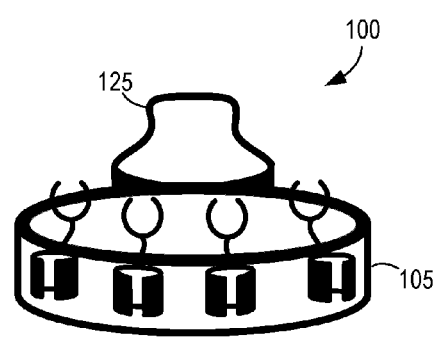
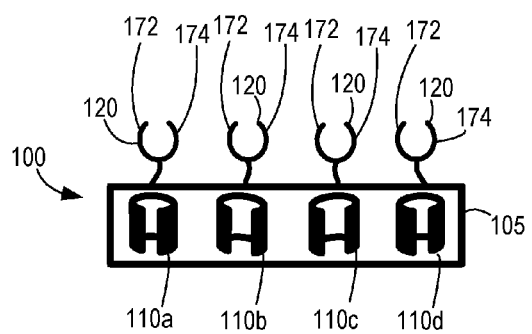
FIG. 1A
FIG. 1B
FIG. 1C

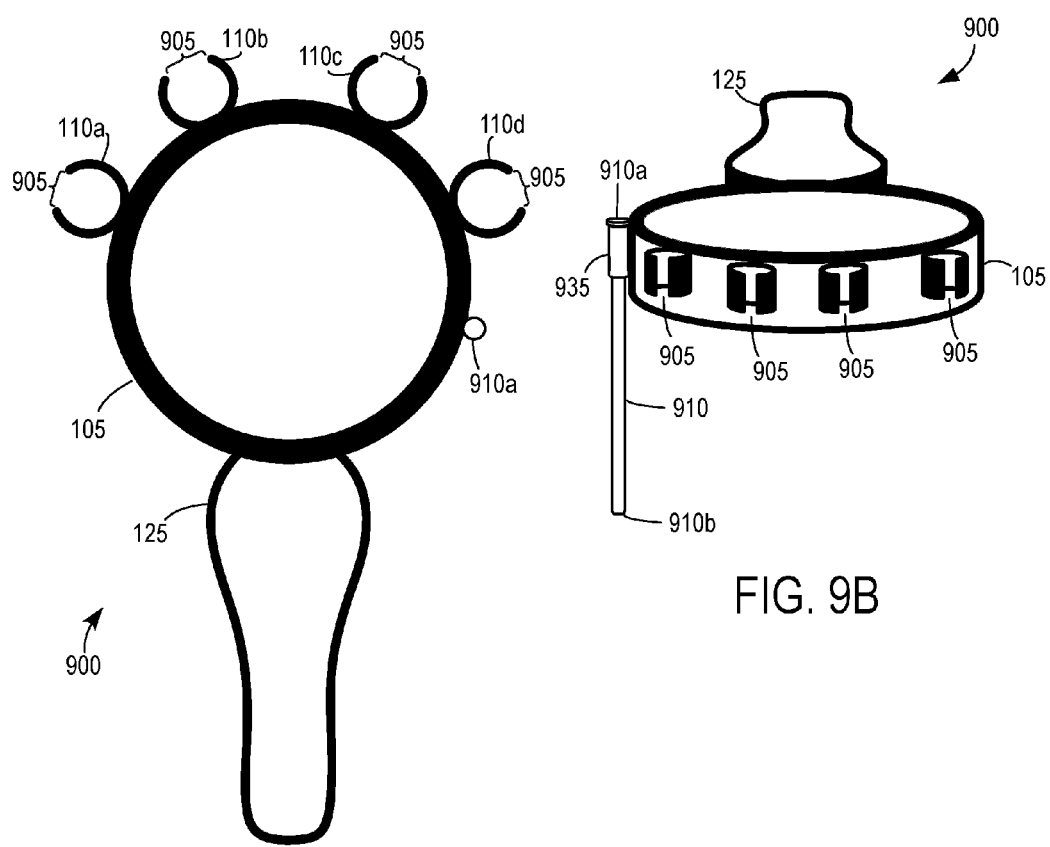

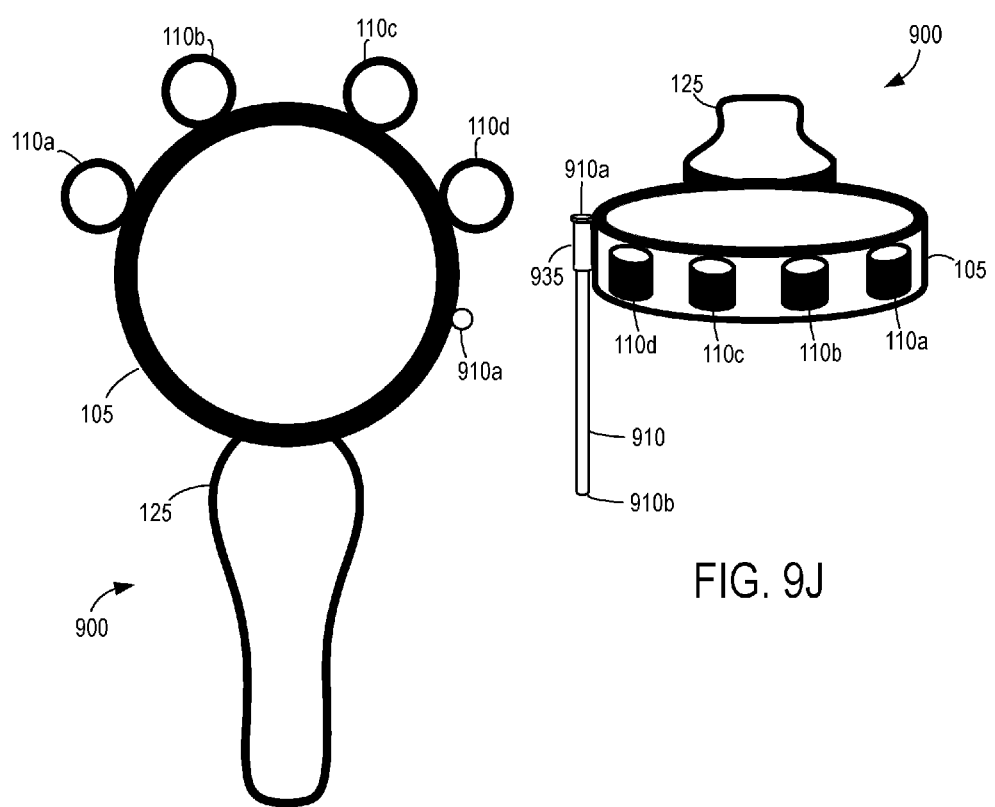

VIAL AND STYLET HOLDER FOR A MEDICAL PROCEDURE

CROSS-REFERENCE TO RELATED APPLICATION

This patent application is a continuation-in-part application of U.S. patent application Ser. No. 14/500,965, filed Sep. 29, 2014, of Dr. Narges Pazouki M.D., titled "Vial and Cap Holder for a Medical Procedure," which is incorporated by reference along with all other references cited in this application.

DESCRIPTION

Background of the Invention

The present invention generally relates to medical instruments used for medical procedures, and more specifically relates to a vial and stylet holder used for a medical procedure.

Medical samples are often taken from a medical patient for diagnosis to determine the patient's health. After a medical sample is taken from a patient, the medical sample is often placed in a container that can be sealed for transport to a diagnostic facility. Containers that used for medical sample storage and transport are typically sterile and are designed to prevent samples from becoming contaminated. After a container with its sample is transported to a diagnostic facility, the sample is removed from the container and is tested according to one or more of a variety of assays.

A vial and a cap used together are one type of container that is often used by medical practitioners for storing and transporting medical samples. A capped vial provides a relatively sterile environment for sample storage and transport.

A medical practitioner using a vial and a cap for sample storage may take a medical sample from a patent, place the medical sample in the vial while the vial is held in one hand, and place the cap on the vial with the other hand. The steps of holding a vial, placing a medical sample inside the vial, and then capping the vial may appear relatively simple, but these steps are often performed while a medical practitioner is performing a medical procedure on a patient. While the medical practitioner is performing the medical procedure, the medical practitioner may also be operating one or more other pieces of medical equipment, interacting with other medical practitioners, and managing the patient. For example, during a lumbar puncture, amniocentesis, paracentesis, or other fluid collection procedure, a puncture needle needs to be managed, a syringe or tubing connected to the puncture needle might need to be managed, and a manometer might be used and need to be managed. Various and other medical devices might also need to be managed while fluid is collected in a vial and then capped. If numerous medical samples are being taken during the medical procedure, then multiple vials and caps might need to be managed while other medical equipment is also managed. These multiple devices and steps being performed substantially simultaneously end up with the simple procedure of placing a medical sample in a vial and capping the vial with a cap relatively complex.

Embodiments of the instant invention are directed at simplifying such medical procedures and thereby improving patient care.

BRIEF SUMMARY OF THE INVENTION

The present invention generally provides a medical instrument used for medical procedures, and more specifically provides a vial and stylet holder used for a medical procedure, such as a lumbar puncture, amniocentesis, paracentesis, or other fluid collection procedure.

According to one embodiment, a vial and stylet holder includes a vial frame and a handle connected to the vial frame. The vial and stylet holder also includes a plurality of vial holders coupled to an outer surface of the vial frame. Each of the vial holders includes a tube. Each tube has an opening formed in a side of the tube that extends from a first end of the tube to a second end of the tube. Each tube is adapted to receive and hold a vial and to flex away from the opening of the tube when a vial is located in the vial holder to exert an inward force on a vial positioned in the tube and flex towards the opening of the tube when a vial is not located in the vial holder.

The vial and stylet holder includes a stylet receptacle coupled to the vial frame. The stylet receptacle includes a tube having an opening at a first end of the tube. A longitudinal axis of the tube of the stylet receptacle is substantially parallel to longitudinal axes of each of the tubes of the vial holders. The stylet receptacle extends past a bottom of the vial frame, and the stylet receptacle is adapted to hold a stylet of a puncture needle.

According to a specific embodiment, the vial frame is a tube and the stylet receptacle is coupled to an outside surface of the tube of the vial frame.

According to another specific embodiment, the vial frame is a tube and the stylet receptacle is coupled to an inside surface of the tube of the vial frame.

According to another specific embodiment, the vial frame has a substantially quadrilateral shape and the stylet receptacle is coupled to an outside surface of the quadrilateral-shape vial frame.

According to another specific embodiment, the vial frame includes a receptacle holder coupled to an outside surface of the tube of the vial frame, and the receptacle holder is adapted to removably receive the stylet receptacle. The receptacle holder includes a tube having a top and a bottom that are open, and a diameter of the receptacle holder is greater than a diameter of the stylet receptacle. Alternatively, the receptacle holder includes a rod having a channel that extends from a top of the rod to a bottom of the rod and the channel is tapered from the top of the rod to the bottom of the rod. The channel has a side opening, a left sidewall, a right sidewall, and a back wall positioned between the left and right side openings. An angle between the left and right sidewalls is greater than zero degrees.

According to another specific embodiment, the stylet receptacle includes a tab having a shape that substantially compliments the channel and the channel is adapted to releasably receive the tab for coupling the stylet receptacle to the vial holder.

According to another specific embodiment, the vial frame is a disk having an aperture formed in the disk adapted to releasably-receive the stylet receptacle.

According to another specific embodiment, the vial and stylet holder includes a plurality of cap holders connected to the vial frame. Each of the cap holders is positioned adjacent to one of the vial holders and is adapted to hold a cap for capping a vial. Each of the cap holders is configured to hold a cap above a top of a vial that is held by one of the vial apertures, and corresponding ones of the vial holders and the cap holders are positioned along common radiuses of the vial frame.

According to one embodiment, a vial and stylet holder includes a vial frame having a rectangular shape and a handle connected to the vial frame. The vial and stylet holder includes a number of vial holders coupled to an outer surface of the vial frame. Each of the vial holders includes a tube that has an opening formed in a side of the tube that extends from a first end of the tube to a second end of the tube. Each of the tubes is adapted to receive and hold a vial and to flex away from the opening of the tube when a vial is located in the vial holder to exert an inward force on a vial positioned in the tube and flex towards the opening of the tube when a vial is not located in the vial holder.

The vial and stylet holder includes a stylet receptacle aperture having a tube shape that is formed in the vial frame. The stylet receptacle aperture extends from a top surface of the vial frame to a bottom surface of the vial frame. A longitudinal axis of the stylet receptacle aperture is substantially parallel to longitudinal axes of each of the tubes of the vial holders. The stylet receptacle extends past a bottom of the vial frame, and the stylet receptacle is adapted to hold a stylet of a puncture needle.

According to a specific embodiment, the vial and stylet holder includes a number of cap holders connected to the vial frame. Each of the cap holders is positioned adjacent to one of the vial holders. Each cap holder is adapted to hold a cap for capping a vial. Each cap holder is configured to hold a cap above a top of a vial that is held by one of the vial apertures, and corresponding ones of the vial holders and the cap holders are positioned along common radiuses of the vial frame.

According to one embodiment, a kit for a lumbar puncture includes a procedure tray comprising a plurality of recesses and a vial and stylet holder positioned in a first recess of the plurality of recesses. The vial and stylet holder includes a vial frame and a handle connected to the vial frame. The vial and stylet holder includes a number of vial holders coupled to an outer surface of the vial frame. Each of the vial holders includes a tube. Each tube has an opening formed in a side of the tube that extends from a first end of the tube to a second end of the tube. Each tube is adapted to receive and hold a vial and to flex away from the opening of the tube when a vial is located in the vial holder to exert an inward force on a vial positioned in the tube and flex towards the opening of the tube when a vial is not located in the vial holder. The vial and stylet holder includes a receptacle holder, having a tube shape, coupled to the vial frame, and includes a stylet receptacle positioned in a second recess of the plurality of recesses. The stylet receptacle includes a tube having an opening at a first end of the tube.

The kit further includes a puncture needle positioned in a third recess of the plurality of recesses. The puncture needle comprises a stylet removably positioned in a central shaft of the puncture needle. The receptacle holder is adapted to removably receive the stylet receptacle and hold the stylet receptacle such that a longitudinal axis of the tube of the stylet receptacle is substantially parallel to longitudinal axes of each of the tubes of the vial holders. The stylet receptacle extends past a bottom of the vial frame when the stylet receptacle is positioned in the receptacle holder. The kit includes an instruction manual for using the kit.

According to a specific embodiment, the kit includes a plurality of vials positioned in corresponding ones of the plurality of recesses.

According to another specific embodiment, the vial frame is a tube and the stylet receptacle is coupled to an outside surface of the tube of the vial frame.

According to another specific embodiment, the vial frame is a tube and the stylet receptacle is coupled to an inside surface of the tube of the vial frame.

According to another specific embodiment, the vial frame is rectangular and the stylet receptacle is coupled to an outside surface of the tube of the vial frame.

According to another specific embodiment, the kit includes a plurality of cap holders connected to the vial frame. Each of the cap holders is positioned adjacent to one of the vial holders. Each cap holder is adapted to hold a cap for capping a vial. Each of the cap holders is configured to hold a cap above a top of a vial that is held by one of the vial apertures, and corresponding ones of the vial holders and the cap holders are positioned along common radiuses of the vial frame.

According to one embodiment, a vial and stylet holder includes a vial frame having a rectangular shape and a handle connected to the vial frame. The vial and stylet holder includes a plurality of vial holders formed in the vial frame where each of the vial holders includes a tube shaped aperture formed in the vial frame. Each tube shaped apertures is adapted to receive a vial. The vial and stylet holder includes a stylet receptacle, having a tube shape, coupled to the vial frame. The stylet receptacle has a longitudinal axis that is substantially parallel to longitudinal axes of each of the tube shaped apertures of the vial holders. The stylet receptacle extends past a bottom of the vial frame, and the stylet receptacle is adapted to hold a stylet of a puncture needle.

According to a specific embodiment, the vial and stylet holder includes a receptacle holder coupled to an outside surface of the vial frame, wherein the receptacle holder is adapted to removably receive the stylet receptacle.

The embodiments described herein provide a number of benefits and advantages for medical personal, medical procedures, and medical patients that will be readily apparent after review of the following detailed description, claims, and appended figures.

BRIEF DESCRIPTION OF THE DRAWINGS

FIG. 1A is a top view of a vial and cap holder according to one embodiment of the present invention.

FIGS. 1B and 1C are a perspective view and a front planar view of the vial and cap holder and show the vial holders attached to an outer surface of the clasp frame according to one embodiment.

FIGS. 9A-9C are a top view, an elevated-front view, and an elevated-side view of a vial and stylet holder according to an embodiment.

FIGS. 9I-9K are a top view, an elevated-front view, and an elevated-side view of a vial and stylet holder having a number of vial holder that are closed tubes according to an embodiment.

DETAILED DESCRIPTION OF THE INVENTION

Figure 2A:
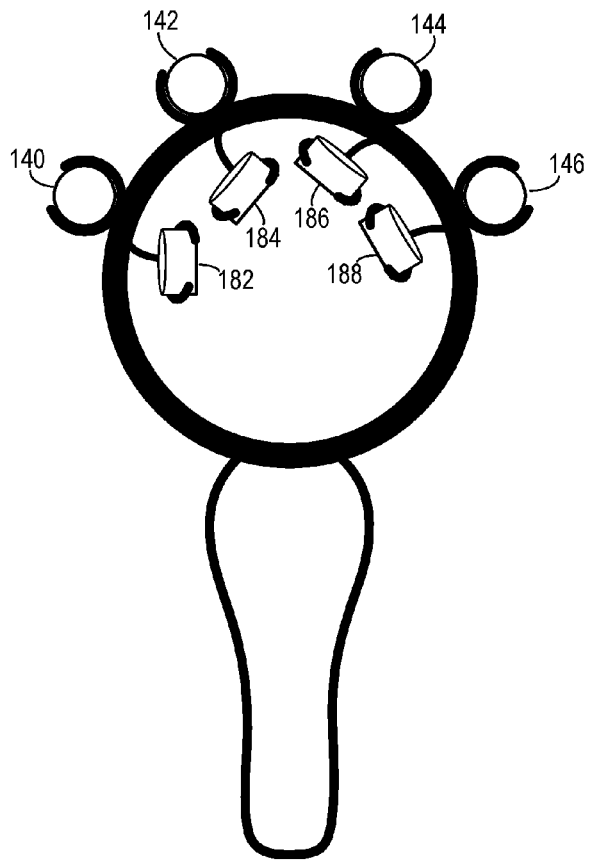
FIGS. 2A, 2B, and 2C are a top view, a perspective view, and a front view of the vial and cap holder holding a number of vials in the vial holders.

The present invention generally provides a medical instrument used for medical procedures, and more specifically provides a vial and cap holder used for a medical procedure, such as a lumbar puncture, amniocentesis, paracentesis, or other fluid collection procedures.

FIG. 1A is a top view of a vial and cap holder 100 according to one embodiment of the present invention. The vial and cap holder includes a clasp frame 105, vial holders 110a, 110b, 110c, and 110d (generally 110), cap holders 120a, 120b, 120c, and 120d (generally 120), and a handle 125. Various embodiments of the vial and cap holder may include one or more of the clasp frame, the vial holders, the cap holders, and the handle in any combination. While the vial and cap holder is shown in FIG. 1A as including four vial holders and four cap holders, the vial and cap holder can include more or less than four vial holders and four cap holders. For example, the vial and cap holder may include two, three, five, six, seven, eight, nine, ten, or more vial holders, and may include a corresponding number of cap holders.

In one embodiment, clasp frame 100 has a generally round shape (e.g., a ring shape, an ellipsoid shape, or other round shape) where a central portion of the clasp frame is open. The clasp frame may be about 1 inch wide to about 6 inches wide with an inner opening of about 0.75 wide inches to about 5.75 inches wide. The clasp frame may have a height of about 0.125 inches to about 1 inch.

Handle 125 may be integrally formed with the clasp frame or may be attached to the clasp frame by a variety of techniques. For example, the handle may be mechanically attached to the clasp frame via rivets, nuts and bolts, screws, slip fit (e.g., tongue and groove), or other devices. The handle may alternatively be attached to the clasp frame via plastic weld (e.g., epoxy or other glue type substance), thermal weld, or other bonding process. The handle may be about 1 inch long to about 6 inches long, and may be about 0.25 inches wide to about 2 inches wide. The handle may be rounded for comfortable holding in a user's hand.

FIGS. 1B and 1C are a perspective view and a front planar view of the vial and cap holder and show the vial holders attached to an outer surface of the clasp frame according to one embodiment. The vial holders may be integrally formed with the clasp frame or may be attached to the clasp frame by a variety of techniques. For example, the vial holders may be mechanically attached the clasp frame via rivets, nuts and bolts, screws, slip fit (e.g., dovetail type joint), or other devices. The vial holders may alternatively be attached to the clasp frame via plastic weld (e.g., epoxy or other glue type substance), thermal weld, or other bonding process.

The vial holders may be attached to the vial and cap holder at a variety of locations along the clasp frame. For example, the vial holders may be located along an arc of about 180 degrees or less, such as an arc of about 90 degrees or less. The vial and cap holder may be separated by 2 inches or less (e.g., 2 inches, 1.75 inches, 1.5 inches, 1.25 inches, 1.0 inches, 0.75 inches, 0.5 inches, or 0.25 inches), or about 40 degrees or less, such as about 30 degrees or less, 25 degrees or less, 20 degrees or less, 15 degrees or less, or 10 degrees or less.

According to one embodiment, each pair of vial holders and cap holders (e.g., pair 1: vial holder 110a and cap holder 120a; pair 2: vial holder 110b and cap holder 120b; pair 3: vial holder 110c and cap holder 120c, and pair 4: vial holder 110d and cap holder 120d) lie along a common line (e.g., a radius) of vial frame 105. The angular separation between the lines (e.g., radiuses) is about 40 degrees or less, such as about 30 degrees or less.

Figure 2B:
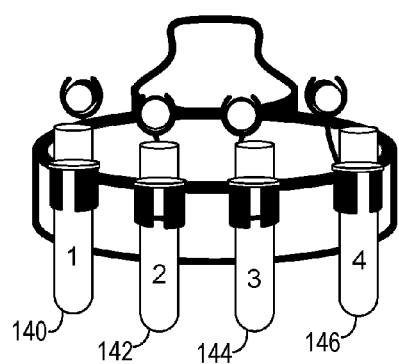
Figure 2C:
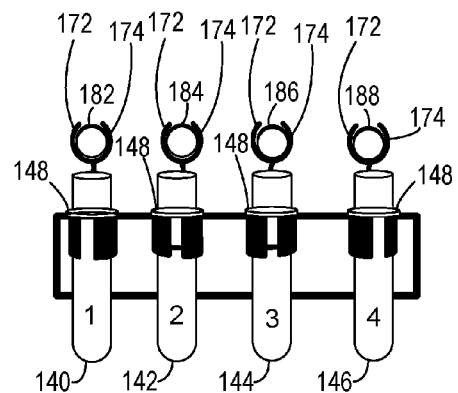

In one embodiment, each vial holder includes a first arm 132 and a second arm 134 where the arms are generally arc shaped and are configured to hold a vial. FIGS. 2A, 2B, and 2C B are a top view, a perspective view, and a front view of the vial and cap holder holding vials 140, 142, 144, and 146 in the vial holders. The vials may be configured for slip on caps, as shown in FIGS. 2A-2C, or may be treaded for receiving threaded caps.

The vial holder may have an inner diameter greater than the outer diameter of the vials or may have an inner diameter less than or equal to the outer diameters of the vials. According to an embodiment where the vial holders have an inner diameter that is greater than the outer diameter of the vials, a vial may be configured to slip into a vial holder and be held in the vial holder by flange 148 on the vial where the flange of the vial contacts the vial holder. Each vial holder has an inner diameter less then a diameter of the flanges so that a flange will contact the vial holder and will not slip down through the vial holder. The inner diameter of the vial holder may be about 0.25 inches or greater, such as about 0.5 inches, 0.75 inches, 1 inch, or greater.

According to an embodiment where the vial holders have an inner diameter that is less than or equal to the outer diameter of the vials, the arms of the vial holders may be configured to flex outward. Specifically, as a vial is pushed into a pair of arms, the arms may flex outward. With the arms in an outward flexed position, the arms exert an inward force on the vial that holds the vial in the arms.

According to one embodiment, each cap holder 120 includes an extension member 150 and a cap clasp 152. Each of the extension members is attached to an inside surface of the vial frame at a first end of the extension member. A second end of the extension member attaches to a corresponding one the cap clasps.

The cap holders 120 may be integrally formed with clasp frame 105 or may be attached to the clasp frame by a variety of techniques. For example, the cap holders may be mechanically attached to the clasp frame via rivets, nuts and bolts, screws, slip fit (e.g., tongue and groove), or other devices. Alternatively, the cap holders may be attached to the clasp frame via plastic weld (e.g., epoxy or other glue type substance), thermal weld, or other bonding process.

In one embodiment, each cap clasp includes a first arm 172 and a second arm 174 where the arms are generally arc shaped and are configured to hold a vial. Each pair of first and second arms meets at a contact location on one of the extensions. FIGS. 2A, 2B, and 2C show the cap clasps holding caps 182, 184, 186, and 188 in arms 172 and 174. While the cap clasps are shown as including first and second arms, the cap clasps may have a variety of alternative shapes for holding the caps. For example, according to an alternative embodiment, the cap clasps may be substantially cylindrical or substantially cylindrical with a side portion opened to allow the cap clasps to bend outward to receive a cap.

Figure 3:
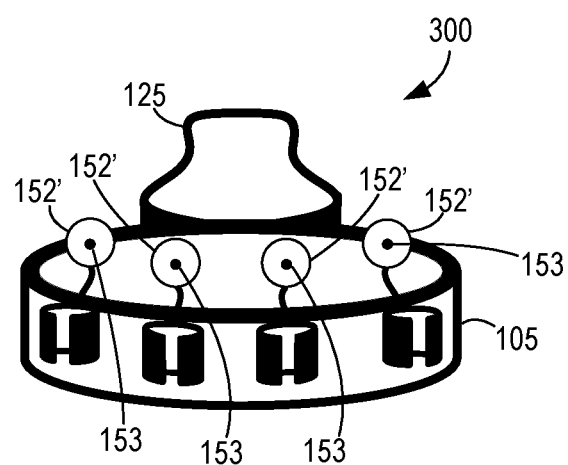
FIG. 3 is a perspective view of the vial and cap holder according to an embodiment where the cap clasps are relatively flat and include one or more adherent devices that respectively adhere the caps to the cap clasps.

FIG. 3 is a perspective view of a vial and cap holder 300 according to an embodiment where the cap clasps 152' are relatively flat and include one or more adherent devices 153 that respectively adhere the caps to the cap clasps. For example, the adherent devices may include an adhesive material where the caps stick to the cap clasps. The adhesive material may be covered by a substantially non-stick material that can be removed from the cap clasp to expose the adhesive material and thereafter the caps may be removably adhered to the adhesive material prior to use of the vial and cap holder. According to another embodiment, the adherent devices includes hook and loop devices, such as Velcro® (a registered trademark of Velcro USA Inc. Manchester N.H.).

According to another embodiment, the adherent devices include a snap device. According to the embodiment, each cap can include a corresponding snap device. The attached snap devices may be configured to allow a cap to rotate while attached to the cap clasp. Providing for the caps to rotate while attached to the cap clasps allows the caps to be threaded onto the vials while attached to the cap clasps. Such attachment provides the benefit, among other things, of allowing a medical practitioner to put a cap fully onto a vial without the chance of a cap being dropped. Snap devices also allow for the caps to be relatively easily unsnapped and unattached from the cap clasps after the caps are threaded onto the vials. The cap clasps and caps can include adherent devices other than snaps that allow the caps to rotate while attached to the cap clasps so that the caps can be threaded onto the veils while attached to cap clasps.

In one embodiment, the vial and cap holders described herein are made at least in part of plastic or other plastic type material, such as nylon, vinyl, acrylic, or other material. The vial and cap holder can also be made of a combination of plastic or plastic type materials. For example, the vial holders and cap clasps may be made of a relatively flexible plastic material, where the clasp frame and handle may be made of relatively rigid plastic material.

Figures 4A, 4B:
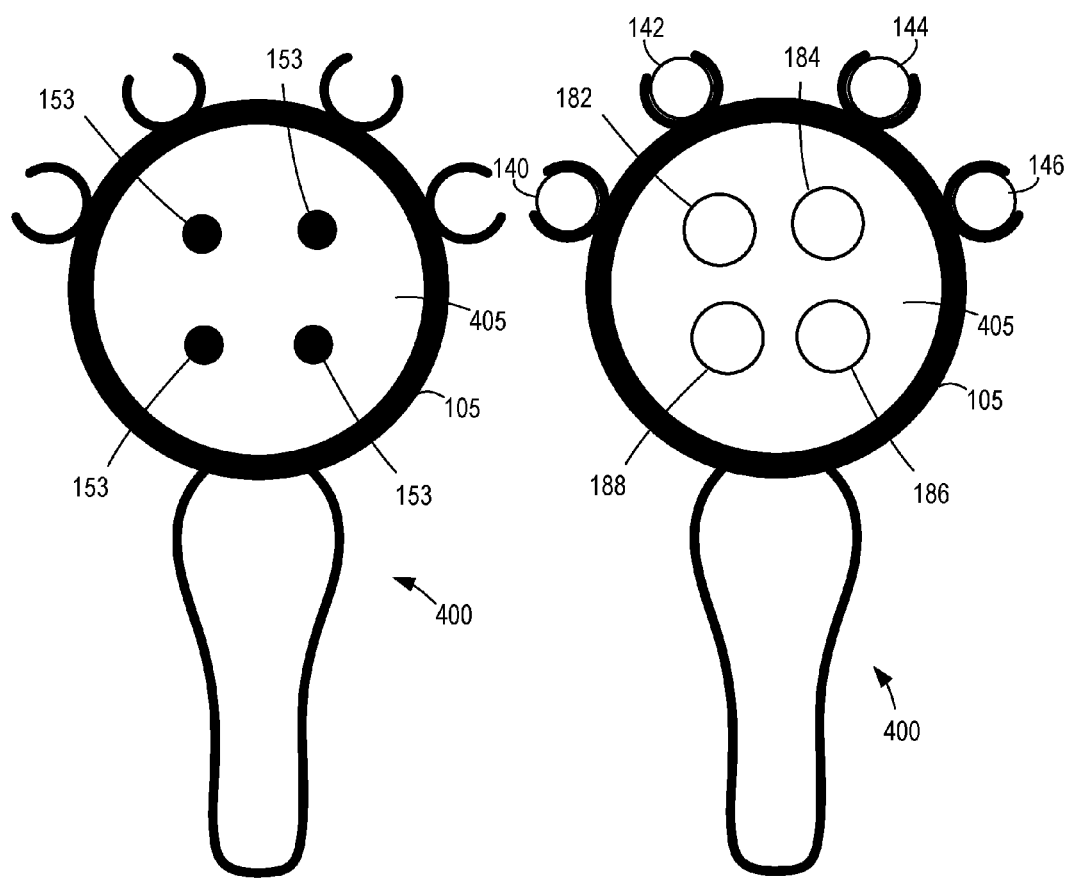
FIGS. 4A and 4B are top views of a vial and cap holder according to another embodiment where the clasp frame includes an inner surface.

FIGS. 4A and 4B are top views of a vial and cap holder 400 according to another embodiment where the clasp frame 105 includes an inner surface 405. The inner surface includes a number of adherent devices 153 positioned on the inner surface where the adherent devices are configured to removably adhere to the caps. FIG. 4B shows a number of caps 182-188 adhered to the adherent devices.

Figure 5:
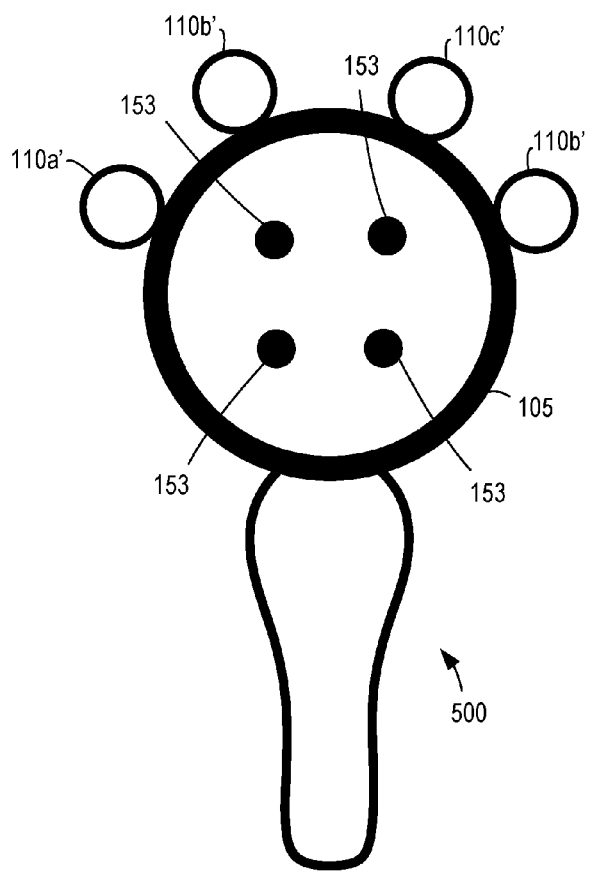
FIG. 5 is a top view of a vial and cap holder according to another embodiment.

FIG. 5 is a top view of a vial and cap holder 500 according to another embodiment. Vial and cap holder 500 includes a number of vial holders 110a', 110b', 110c', and 110d' where the vial holders have a closed shape. The closed shape can be substantially round, such as circular, for holding a set of vials. While vial and cap holder 500 is shown in FIG. 5 as including adherent devices 153 for holding the caps, the vial and cap holder can include cap clasps as shown in FIGS. 1A-1C or otherwise as described herein.

The closed shaped vial holders may have an inner diameter that is larger than the outer diameter of the vials that are configured to be held by the vial holders. Flanges of the vials may be configured to contact the vial holders to hold the vials in the vial holders.

Figure 6:
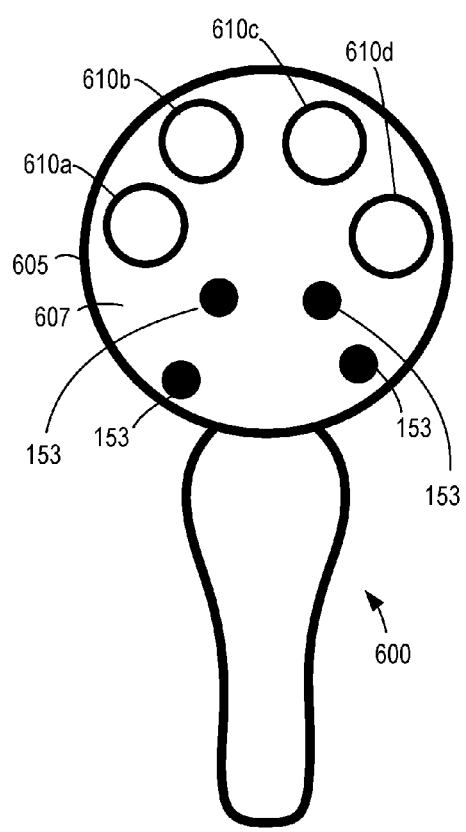
FIG. 6 is a top view of a vial and cap holder according to another embodiment.

FIG. 6 is a top view of a vial and cap holder 600 according to another embodiment. Vial and cap holder 600 includes a vial frame 605 that has an inner surface 607. Inner surface 607 has a number of vial apertures 610a, 610b, 610c, and 610d (generally 610) formed in the inner surface. The vial apertures are configured to receive and hold a set of vials. Each vial aperture has a diameter that is greater than the diameter of the vials and less than the diameter flanges of the vials so that the flanges can contact inner surface 607 with the vials positioned in the apertures. While vial and cap holder 600 is shown as having four vial apertures, the vial and cap holder can have more or fewer vial apertures configured to hold vials.

Apertures 610 can be substantially round, such as circular, for holding a set of vials. While vial and cap holder 600 is shown in FIG. 6 as including adherent devices 153 for holding the caps, the vial and cap holder can include other cap holders, such as the cap holders shown in FIGS. 1A-1C, FIG. 3, or otherwise as described herein. The cap holders can be positioned on a side of the vial frame where the cap holders can be configured to hold the caps adjacent to the tops of the vials while the vials are positioned in the vial apertures.

Figure 7:
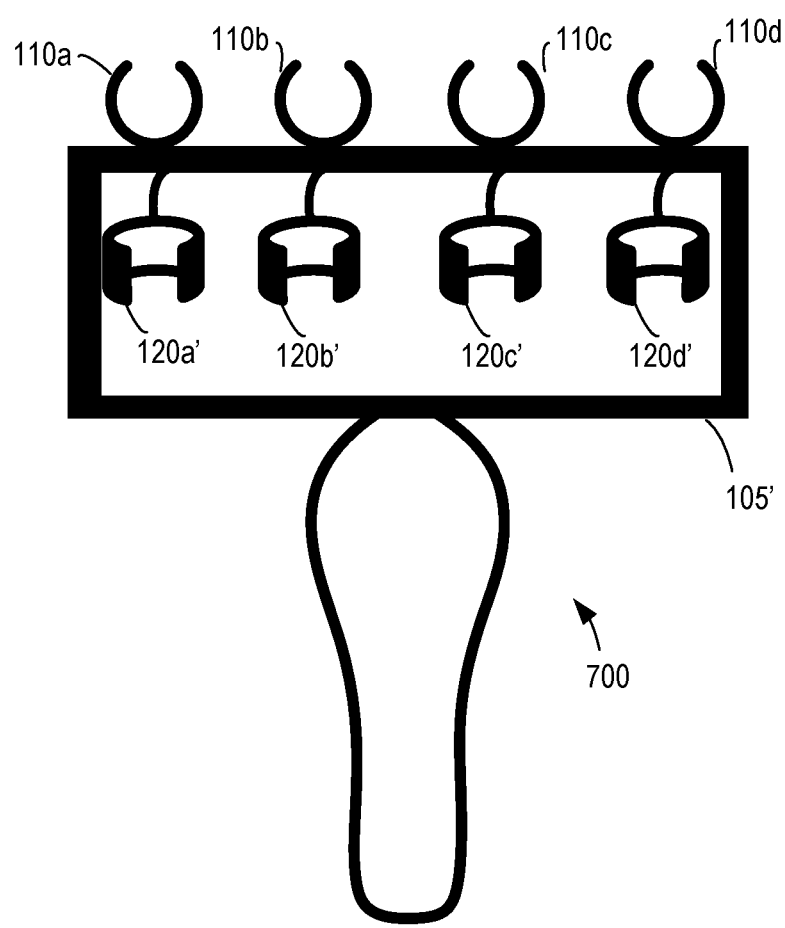
FIG. 7 is a top view of a vial and cap holder according to another embodiment.

FIG. 7 is a top view of a vial and cap holder 700 according to another embodiment. Vial and cap holder 700 is substantially similar to vial and cap holder 100 but vial and cap holder 700 has a clasp frame 105' that is quadrilateral shaped from a top and bottom view, such as a parallelogram shape, a rectangular shape, or a square shape. While clasp frame 105' is shown as being quadrilateral, the clasp frame can have a variety of other shapes, such as capricious, triangular, pentagonal, or other shapes.

Vial and cap holder 700 also has a number of cap clasps 120a', 120b', 120c', and 120d' that are substantially cylindrical in shape with a side portion that is open to allow the cap clasps to flex outward when caps are placed in the cap clasps. The outward flex provides that an inward force is placed on the caps to hold the caps in place.

According to one alternative embodiment, the caps are attached to the vials, and the embodiments described herein do not include cap holders. The caps can be mounted on the vials for rotating a cap from a side position on a vile to being positioned over the top of the vial for capping the vial.

The vial and cap holders described herein provide a number of benefits for patients and for medical practitioner who take fluid samples and tissue samples from patients. The vial and cap holders provide that a medical practitioner can relatively easily and quickly move the vials into position, for example, at the end of a puncture needle, for taking fluid samples without a patient losing excessive amounts of fluid (e.g., cerebrospinal fluid). For example, during a lumbar puncture, a doctor while holding the vial and cap holder can relatively quickly move the openings of successive vials to the end of the puncture need to capture cerebrospinal fluid to substantially minimize the amount of time that cerebrospinal fluid is collected from the lumbar puncture.

In contrast, during a traditional method of collecting cerebrospinal fluid from a lumbar puncture each vial and cap is handled independently by a doctor. For example, each vial and cap is removed independently from a procedural tray and placed back in the procedural tray after a sample is taken and a vial is capped. More specifically, a first vial may be removed from the procedural tray, the first vial may be moved to the end of the puncture needle where a sample is collected in the first vial, a first cap is then removed from the procedural tray, the vial is capped, and the capped vial is returned to the procedural tray. These steps are repeated for each vial and cap (e.g., often four vials and four caps) while the patients continues to lose cerebrospinal fluid and while the doctor continues to manage the patient, staff, and other pieces of medical equipment in the operating room. Handling each vial and cap independently allows a relatively large amount of cerebrospinal fluid to go un-captured from the puncture needle.

The vial and cap holders described herein allow for relatively minimal loss of uncollected cerebrospinal fluid during a lumbar puncture and thereby provide patients a number of benefits including lowering the patient's likelihood of getting a headache from excessive loose of cerebrospinal fluid or other body aches associated with cerebrospinal fluid loss. The vial and cap holders described herein also allow for a puncture needle to be in place in a patient for a shorter time compared to traditional methods of fluid collection where vials and caps are independently handled over a longer period of time for fluid capture.

Often, if relatively large amounts of cerebrospinal fluid leak from a spinal puncture, a patient will be admitted to the hospital for a relatively extended stay that can last for one to several days. Such extended hospital stays are relatively costly, which embodiments of the current invention can limit by limiting the amount of cerebrospinal fluid that leaks from a spinal puncture, thereby saving hospitals, patients, and medical insurance providers money.

The vial and cap holders described herein further provide for a relatively high likelihood of keeping collected sample sterile due the caps for the vials being positioned adjacent to the top openings of the vials on the vial and cap holder. The positioning of a cap adjacent (e.g., 1.5 inches or less, such as 1.25 inches, 1.0 inches, 1.75 inches, 1.5 inches, 1.25 inches, 1.0 inches, 0.75 inches, 0.5 inches, 0.25 inches, 0.2 inches, 0.1 inches) to the top of a corresponding vial provides that each cap can be relatively quickly accessed and thereby the vials can be relatively quickly capped. Quick capping of the vials limits the amount of time that collected sample are exposed to the air of the ambient environment and thereby limits that likelihood that contaminants, such as bacteria, can enter the vials prior to capping. The capped vials can thereafter be removed from the vial and cap holder and sent to a lab for analysis of the samples.

The vial and cap holders described herein also decrease health risks for medical personal who collect patients bodily fluids because individual vials do not need to be held by hand when fluid sample are collected in a vial. Holding the vials at the end of a vial and cap holders while collecting a bodily fluid sample lowers the chance that the bodily fluid will contact a care providers hand or other body parts. Often, samples of bodily fluid are contagious, some highly contagious, and put medical personal at risk of exposure to the samples. For example, in cases were a patient has Creutzfeldt-Jakob disease (CJD), which is a type of mad caw disease, cerebrospinal fluid samples are very contagious, and holding a number of vials with a vial and cap holder described herein can reduce the likelihood that medical personal will contact the vials. According to some embodiments, a procedural tray (described below) is provided in which capped vials can be placed without medical personal contacting the vials while the vials are held by the vial and cap holder and while a care provider holds the handle of the vial and cap holder.

Figure 8:
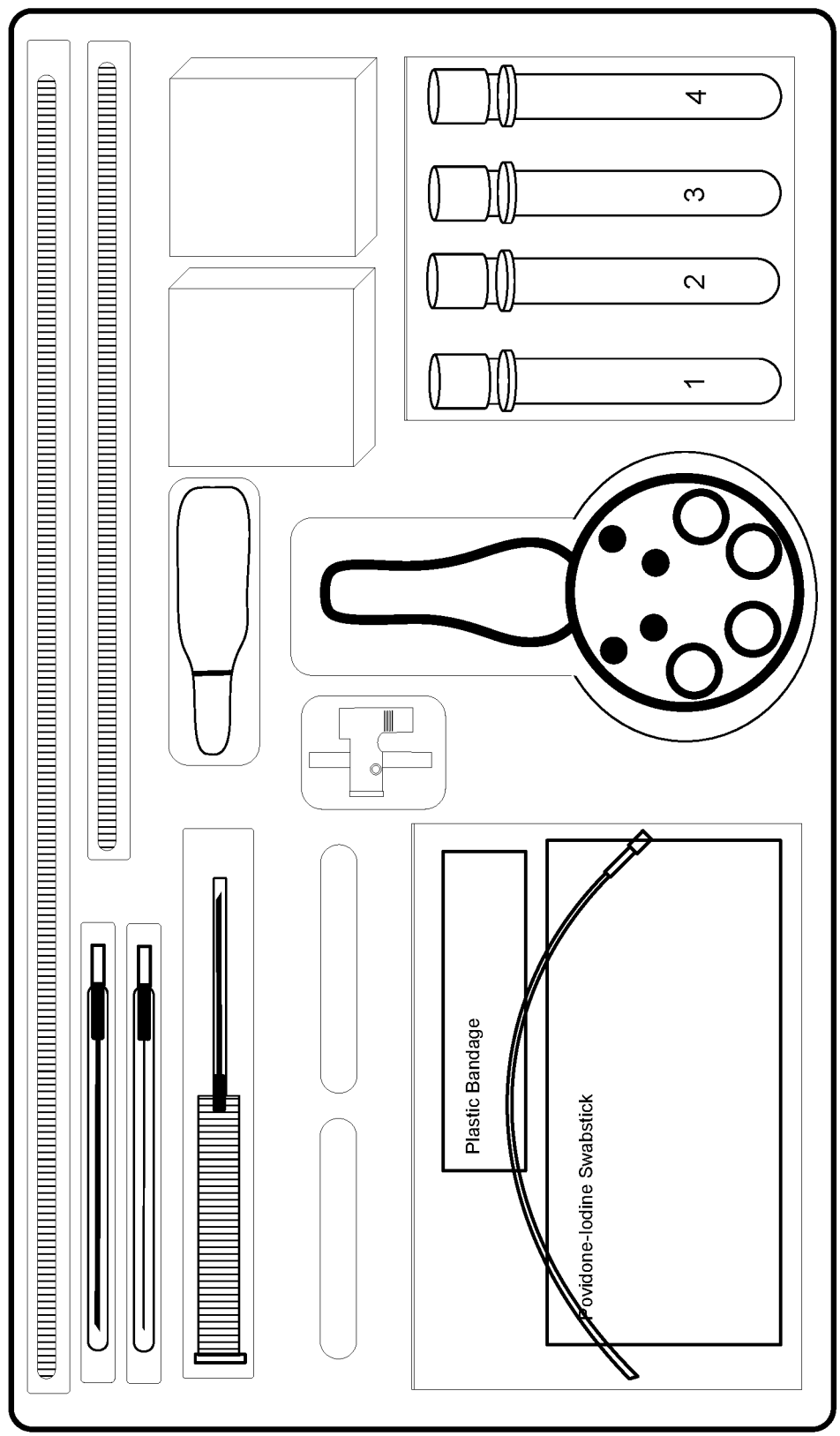
FIG. 8 is a diagram of a procedural tray according to one embodiment.

FIG. 8 is a diagram of a procedural tray according to one embodiment. The procedural tray includes a first portion (e.g., a recessed portion) that is configured to contain the vial and cap holder, and a second portion (e.g., a recessed portion) that is configured to contain the vials and caps. The procedural tray may be a lumbar puncture tray or a tray for a different procedure. While the procedural tray is shown as including a vial and cap holder that is configured to hold four vials and four caps, the vial and cap holder may be configured to hold more or fewer vials and caps. The procedural tray may be plastic and the recessed portions may be in the general shape of the objects being held. The procedural tray may include other items such as various size puncture needles, a syringe, or the like. According to one embodiment, the procedural tray includes a third portion having a number of receptacle portions that are configured to receive the capped vials from the vial and cap holder. The receptacle portions may include recesses, such as four recesses, into which the capped vials held by the vial and cap holder can be placed. The receptacle portions may have a shape (curved or straight) that matches the positions of the vial holders in the vial and cap holder. A user may position the bottom of the vials in the receptacle portions and the vials may thereafter be held by the receptacle portions. The procedural tray may be packaged and then transferred to a lab providing for substantially minimal contact with the vials while sample are collected.

Figure 9C:
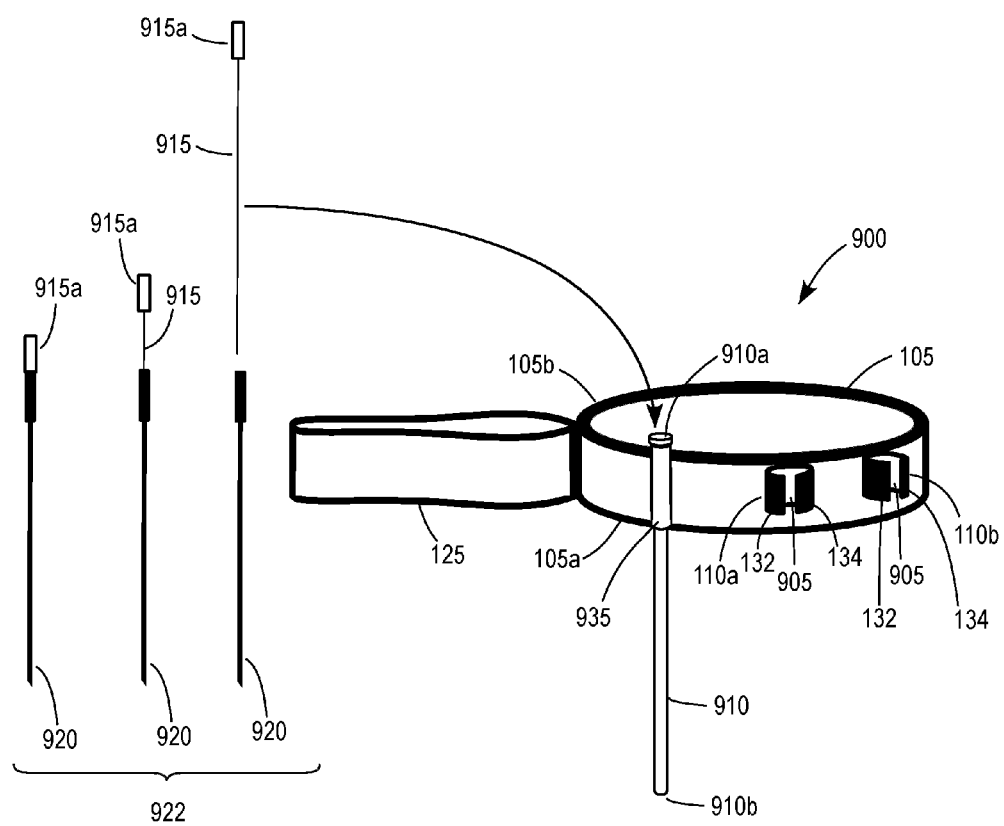

FIGS. 9A-9C are a top view, an elevated-front view, and an elevated-side view of a vial and stylet holder 900 according to an embodiment. Vial and stylet holder 900 includes a number of vial holders, such as four vial holders 110a, 110b, 110c, and 110d. The vial holders may have any of the shapes, sizes, and dimensions described above. For example, each vial holder may include a tube where each tube has a side opening 905 (e.g., a rectangular-shaped side opening) and where each side opening is between a first arm 132 and a second arm 134 of the tube. In some embodiments, the vial and stylet holder also includes a number of cap holders (not shown).

Figure 9D:
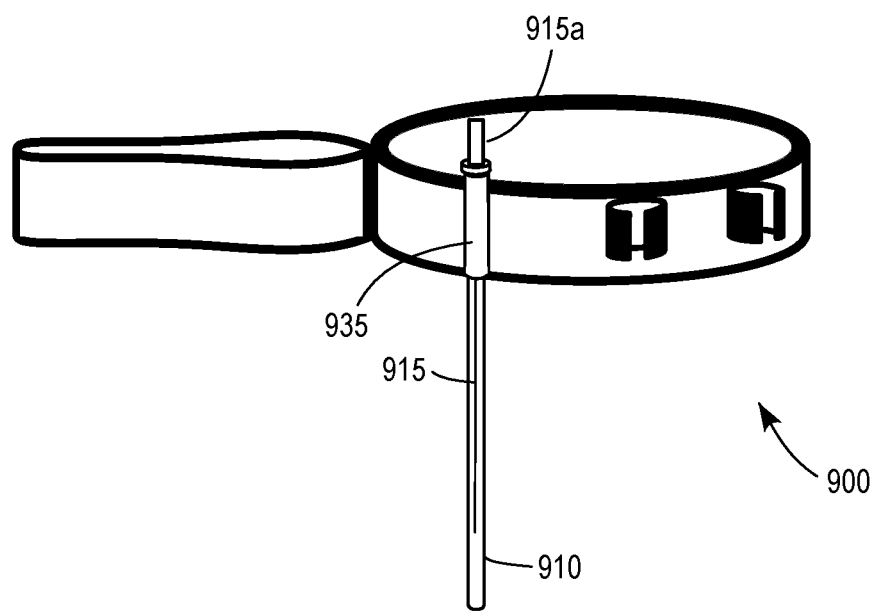
FIG. 9D shows the stylet positioned in the stylet receptacle.

Vial and stylet holder 900 includes a stylet receptacle 910 that is adapted for holding a stylet 915. Stylet 915 can be the stylet of a puncture needle 920. Puncture needle 920 can be adapted for a lumbar puncture for sampling cerebrospinal fluid of a patient, such as a human patient, or can be adapted for other medical procedures. FIG. 9C shows a timed sequence of events 922 of the stylet being removed from the puncture needle in preparation to place the stylet into the stylet receptacle. FIG. 9D shows the stylet positioned in the stylet receptacle.

During use of the puncture needle, when the tip of the puncture needle is inserted into a portion of a patient's body, such as when the puncture needle is inserted into the subarachnoid space of a patient's spinal column to collect cerebrospinal fluid, the stylet is positioned in an inner shaft of the puncture needle. When the stylet is positioned in the inner shaft of the puncture needle, the stylet inhibits cerebrospinal fluid from passing through the needle. Thereafter, when cerebrospinal fluid, for example, is to be collected via the puncture needle, the stylet is removed from the puncture needle. When the stylet is removed from the puncture needle the cerebrospinal fluid to allowed to flow through the puncture needle for collection. When the cerebrospinal fluid is finished being collected, the stylet is placed back into the puncture needle to stop the flow of cerebrospinal fluid from the needle.

After the cerebrospinal fluid is collected, if the stylet is not retrieved relatively quickly and positioned back into the inner shaft of the puncture needle, then cerebrospinal fluid will leak unnecessarily through the needle from the patient's subarachnoid space. Therefore, quickly retrieving the stylet is desired so that the stylet can quickly be placed back into inner shaft the puncture needle to stop the flow of cerebrospinal fluid through the puncture needle.

With the stylet positioned in the stylet receptacle of the vial and stylet holder, the stylet can be in the practitioner's hand by holding the vial and stylet holder, can be in the practitioner's hand by holding the vial and stylet holder within view, or both. Therefore, the stylet can quickly be located and positioned in the puncture needle. The stylet can be located relatively quicker then if the stylet is placed in the procedural tray or another location that is out of direct view of the practitioner, away from the puncture needle, or both. Further, with the stylet in the stylet holder, the handle 915a of the stylet is oriented upward in the vial and stylet holder for easy and quick grasping by a practitioner.

In an implementation, the stylet receptacle 910 is a tube that has an opening at a top 910a of the tube. A bottom 910b of the tube may be open or closed. The bottom of the tube extends past a bottom 105a of the vial holder. The top of the tube can be above, level with, or below the top 105b of the vial holder. In one implementation, the tops and bottoms of the tubes of the vial holders do not extend past the top and bottom of the vial frame.

The tube of the stylet receptacle has a longitudinal axis that extends from the top of the tube to the bottom of the tube. The longitudinal axis of the tube of the stylet receptacle is substantially parallel to longitudinal axes of the tubes of the vial holders where the longitudinal axes of the tubes of the vial holders, respectively, extend from the tops of the tubes of the vial holders the bottoms of the tubes of the vial holders.

The tube of the stylet receptacle may have a variety of lengths for holding stylets having a variety of lengths. For example, the tube can have lengths that range from about one into about twelve inches. Generally, shorter length tubes, for example, about three inches or less can hold stylets used with puncture needles that are designed for use with babies, children, or relatively small adults. Generally, medium length tubes, for example, about three inches to about six inches can hold stylets used with puncture needles that are designed for use with adults. Generally, longer tubes, for example, six inches and longer can hold stylets used with puncture needles that are designed for use with relatively large adults.

The top opening of the tube, into which the stylet slides into and out from, may have a diameter of about one sixteenth of an inch to about one quarter of an inch or larger. For example, the diameter of the top opening of the tube can one sixteenth of an inch, one eighth of an inch, three sixteenths of an inch, one quarter of an inch, five sixteenths of an inch, three eighths of an inch, or greater.

The tube can be formed of one or more of a variety of materials, such as one or more of a variety of plastics, plastic type materials, metal, or other materials. The tube can be relatively transparent or opaque.

The top of the tube may include a flange 915c that has a diameter that is greater than the diameter of the tube and greater than the diameter of the stylet receptacle. The flange may have a variety of heights, such as one sixty-fourth of an inch, one sixteen of an inch, one eighth of an inch, three sixteenth of an inch, one quarter of an inch, or greater. The flange may be attached to the tube via a variety of methods and materials, such as plastic welding, glue, epoxy, integrally molded with the tube, or other methods.

In an implementation, the stylet receptacle is separable from the vial and stylet holder. For example, the vial and stylet holder may include a receptacle holder 935, such as a tube, that is adapted to receive the stylet receptacle. The receptacle holder can be attached to clasp frame 105 at a side of the clasp frame, such as an outer side of the clasp frame as shown in FIG. 9D or an inner side of the clasp frame as shown in FIG. 9D, for example if the clasp frame is a tube having an inner portion that is open. A diameter of the receptacle holder is greater than a diameter of the stylet holder and less than the diameter of the stylet holder's flange.

Figure 9E:
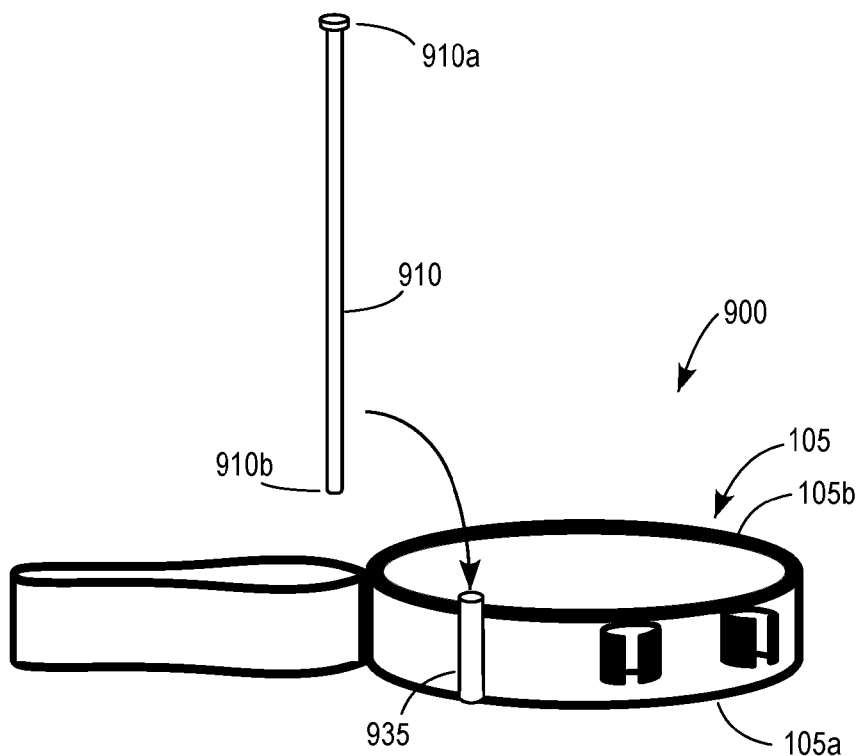
FIGS. 9E-9F show a time sequence of events of the stylet receptacle be separated from the receptacle holder to the stylet receptacle being positioned the receptacle holder where the receptacle holder is coupled to an outer side of the clasp frame.
Figure 9F:
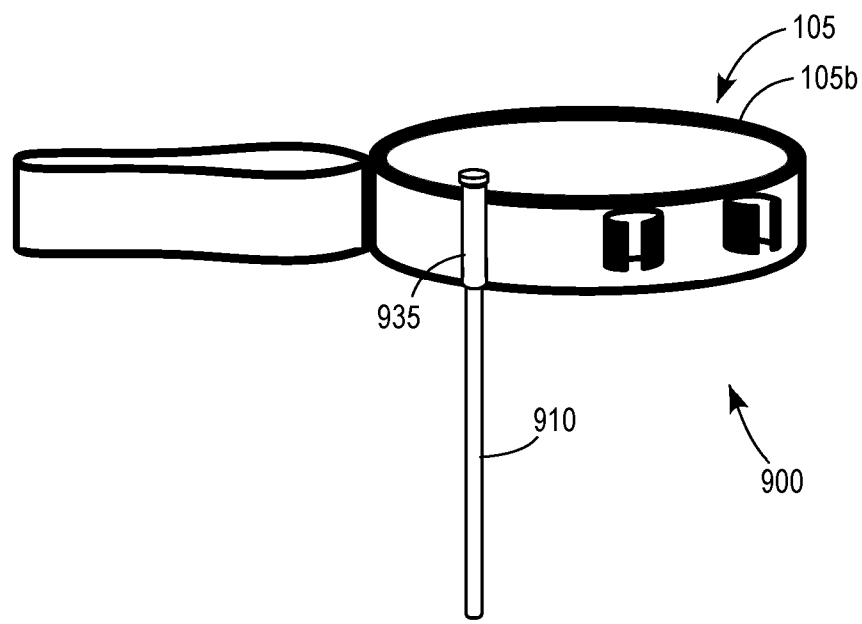

FIGS. 9E-9F show a time sequence of events of the stylet receptacle be separated from the receptacle holder to the stylet receptacle being positioned the receptacle holder where the receptacle holder is coupled to an outer side of the clasp frame.

Figure 9G:
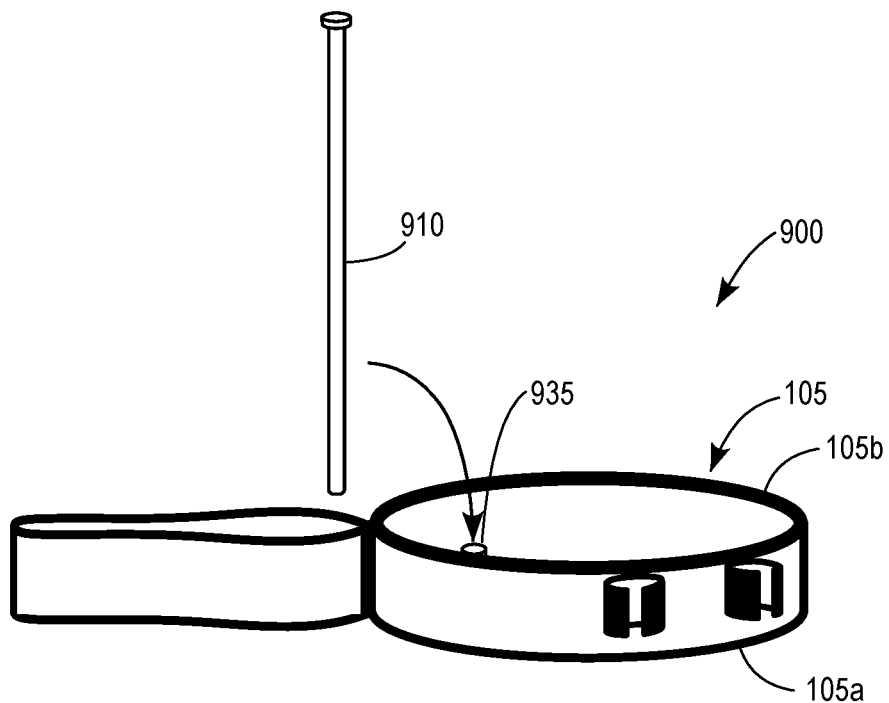
FIGS. 9G-9H show a time sequence of events of the stylet receptacle be separated from the receptacle holder to the stylet receptacle being positioned the receptacle holder where the receptacle holder is coupled to an inside side of the clasp frame.
Figure 9H:
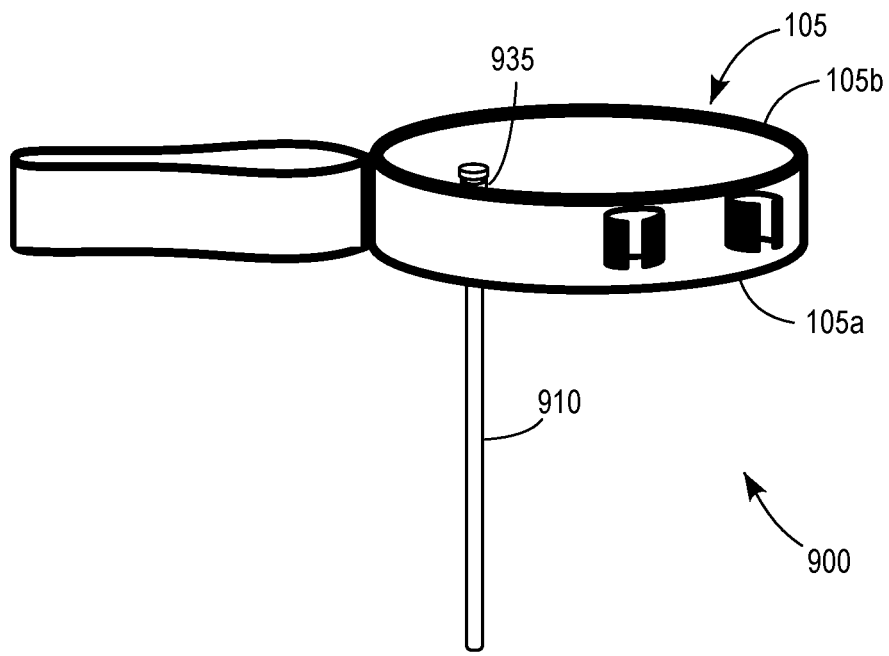

FIGS. 9G-9H show a time sequence of events of the stylet receptacle be separated from the receptacle holder to the stylet receptacle being positioned the receptacle holder where the receptacle holder is coupled to an inside side of the clasp frame.

Figure 9K:
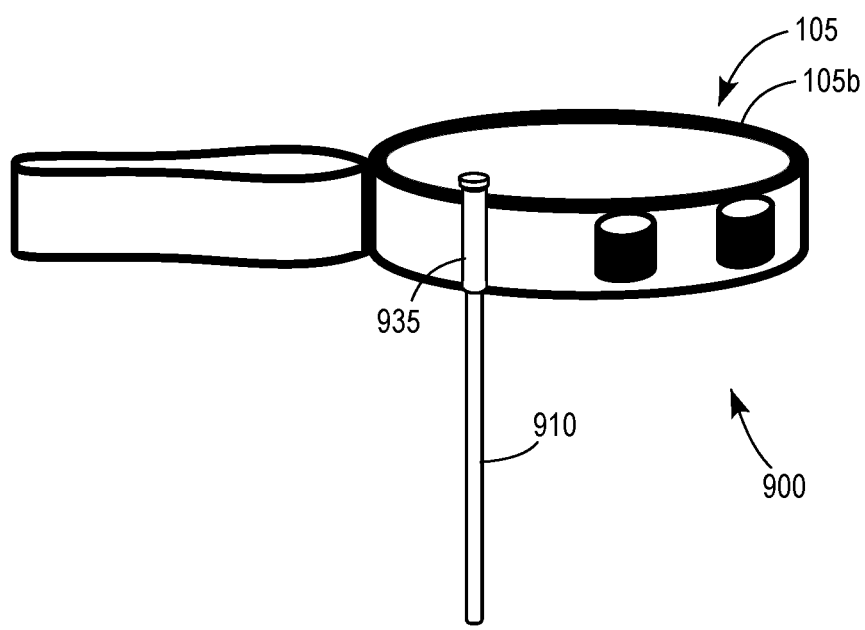

FIGS. 9I-9K are a top view, an elevated-front view, and an elevated-side view of a vial and stylet holder 900 according to an embodiment where each of the four vial holders 110a, 110b, 110c, and 110d include closed tubes. That is, the closed tubes have top and bottom openings for receiving vials, but the closed tubes do not have side openings side opening 905 as described above and shown in FIGS. 9A-9C. The top and bottom openings of the closed tubes are substantially circular. The elevated-front view and the elevated-side view of the vial holders are shown as oblong in FIGS. 9B-9C due to the elevated views. The top and bottom openings of the closed tubes are shown as substantially circular in FIG. 9A.

Figure 9L:
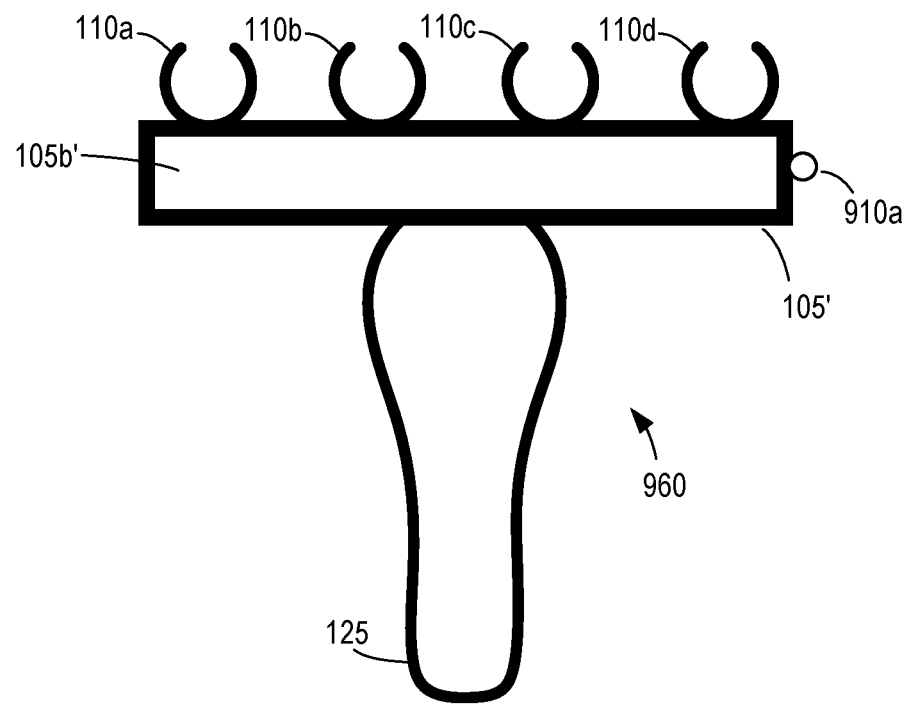
FIGS. 9L-9N are a top view, an elevated-front view, and an elevated-side view of a vial and stylet holder according to an embodiment of the present invention where the clasp frame is a polygon.
Figure 9M:
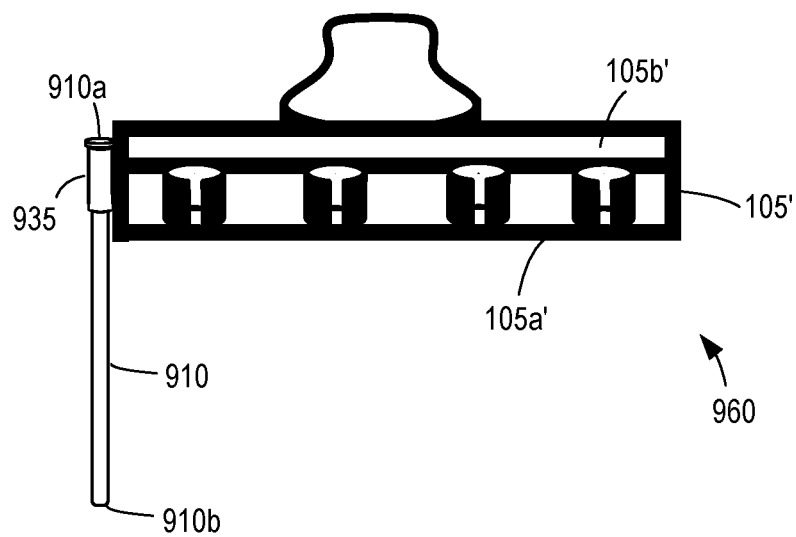
Figure 9N:
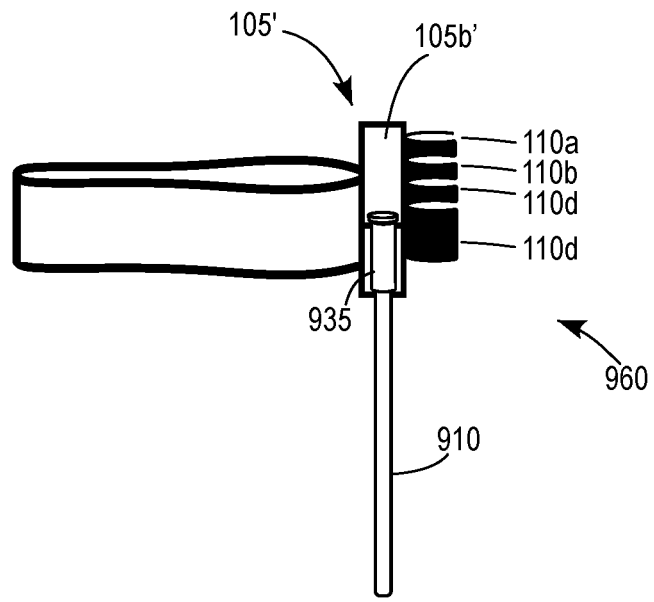
Figure 9O:
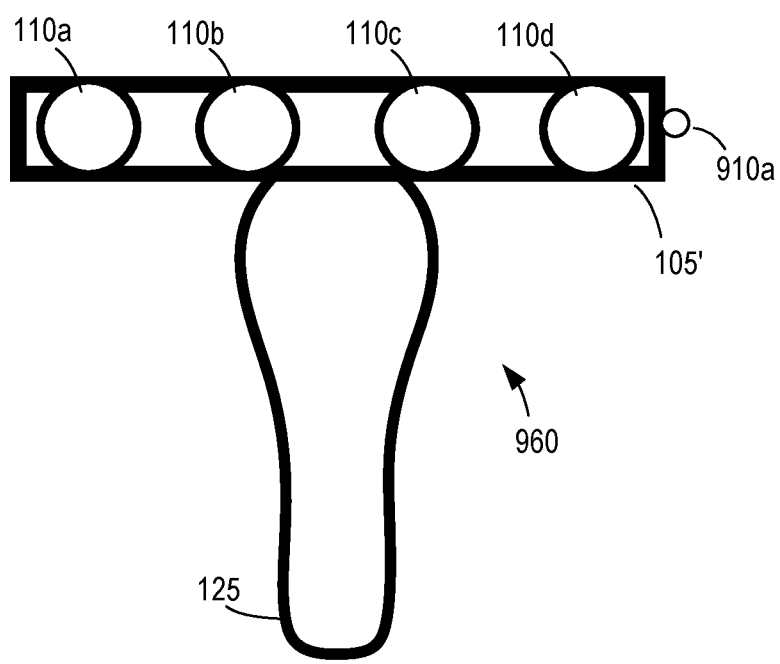
FIG. 9O is a top view of a vial and stylet holder according to an embodiment of the present invention where the vial holders include apertures formed in the clasp frame.

FIGS. 9L-9N are a top view, an elevated-front view, and an elevated-side view of a vial and stylet holder 960 according to an embodiment where the clasp frame 105' is a polygon, such as a rectangle. The clasp frame 105' is attached to the handle 125 and holds the vial holders 110a-110d, with the clasp frame positioned between the handle and the vial holders. In some embodiment, the vial holders are apertures formed in the clasp frame as shown in FIG. 9O. The vial holders can be tube shaped with side openings 905 or tube shaped without a side openings, such as described above and shown in FIGS. 9I-9K.

The receptacle holder 935 may be attached to an outside surface of the clasp frame 105' or the receptacle holder can be an aperture formed in the clasp frame as described above and as shown in FIGS. 9G-9H. In some embodiments, the receptacle holder is attached to handle 125 or is formed in the handle as an aperture.

Figure 10A:
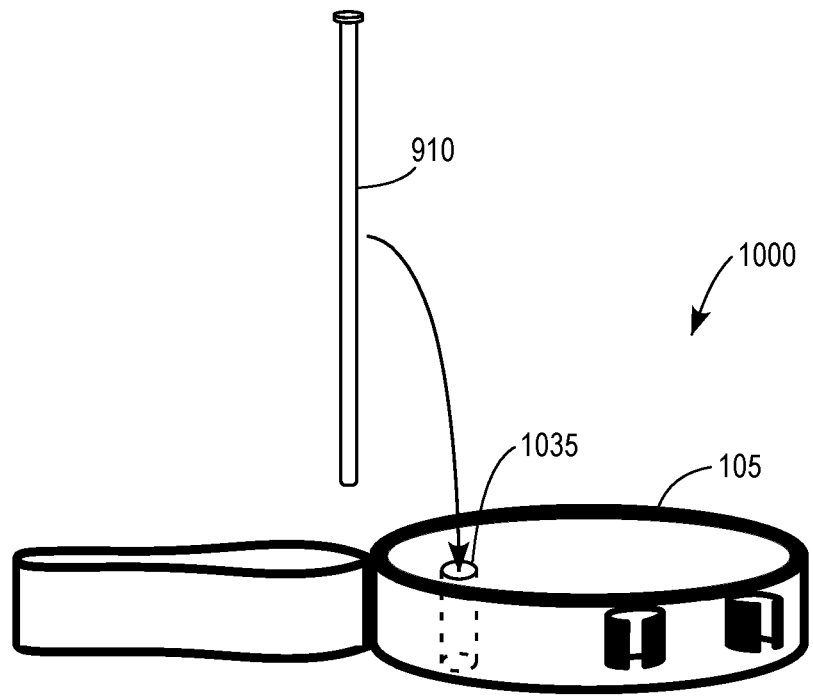
FIGS. 10A-10B show a vial and stylet holder where the clasp frame is a disk.
Figure 10B:
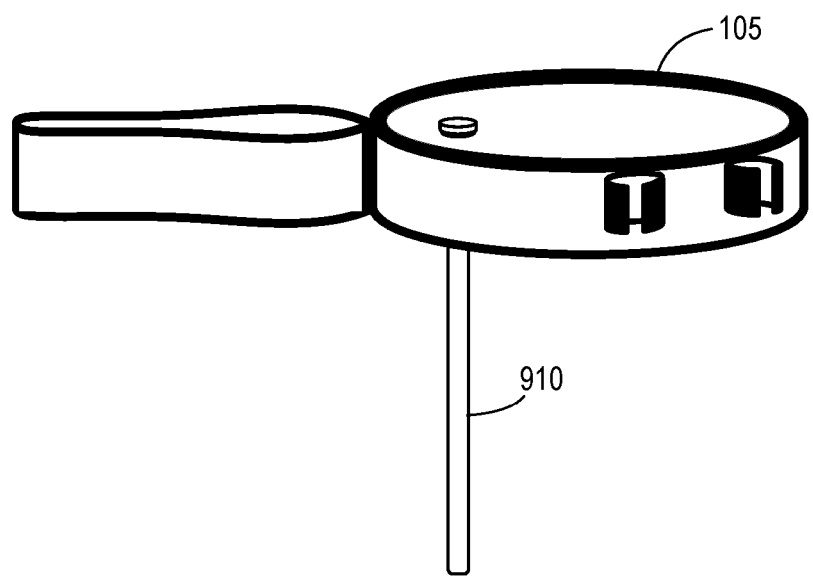

FIGS. 10A-10B show a vial and stylet holder 1000 where the clasp frame 105 is a disk. The clasp frame has an aperture 1035 formed in the clasp frame where the aperture is the receptacle holder adapted for receiving stylet receptacle 910. FIG. 10A shows the portion of the aperture extending through the clasp frame as a dashed line.

In an alternative embodiment, the clasp frame is a tube with an open center, such as shown in FIG. 9B, where the wall of the tube is relatively thick and the aperture that is the receptacle holder is formed in the wall of the tube of the clasp frame. In an implementation, the vial holders are formed as apertures in the disk and are not coupled to an outside surface of the disk (see FIG. 12).

Figure 11:
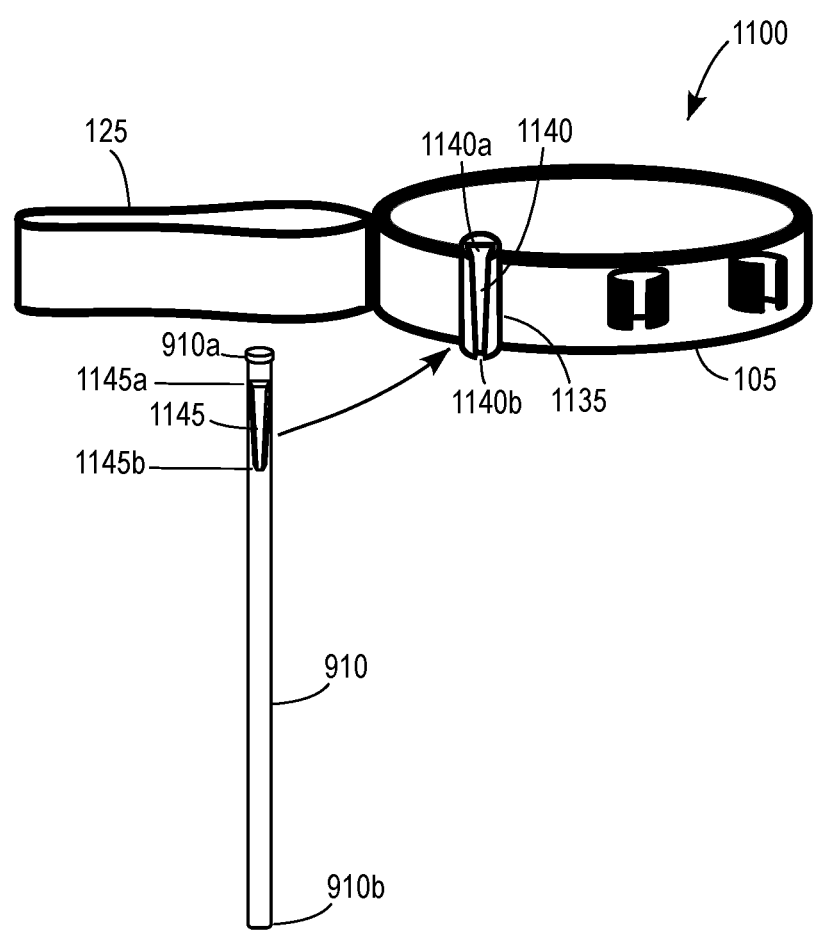
FIG. 11 shows an elevated-side view of a vial and stylet holder in an embodiment.

FIG. 11 shows an elevated-side view of a vial and stylet holder 1100 in an embodiment. The vial and stylet holder includes a receptacle holder 1135 that includes a rod. A channel 1140 formed in the rod extends from the top of the rod to the bottom of the rod. The channel can have a shape that is substantially complimentary to a shape of a tab 1145 that is positioned on a side of the tube of stylet receptacle 910. The tab can be fitted into the channel such that the channel holds that tab and inhibits the tab from sliding outward from the bottom of the channel. The channel may have a variety of shapes, such as an outward-angled trench. For the outward-angled trench, the left and right sides of the channel are angled at greater than ninety degrees with respect to a side opening of the channel. That is, the left and right sidewalls are not parallel and are angled at greater than zero degrees with respect to each other. In an implementation, the outward-angled trench tapers from a top 1140a of the outward-angled trench to a bottom 1140b of the outward-angled trench. The shape of the tab can substantially compliment the shape of the outward-angled trench, where the tab may be an outward-angled tab that tapers from the top 1145a of the tab to the bottom 1145a of the tab.

Receptacle holder 1135 can be coupled (e.g., directly connected) to an outer side surface of clasp frame 105 or can be coupled (e.g., directly connected) to an inner side surface of clasp frame 105 where the clasp frame is a tube having a central opening. In some embodiments, the receptacle holder is formed in the handle 125 or is coupled (e.g., directly attached) to an outer or inner surface of the handle.

Figure 12:
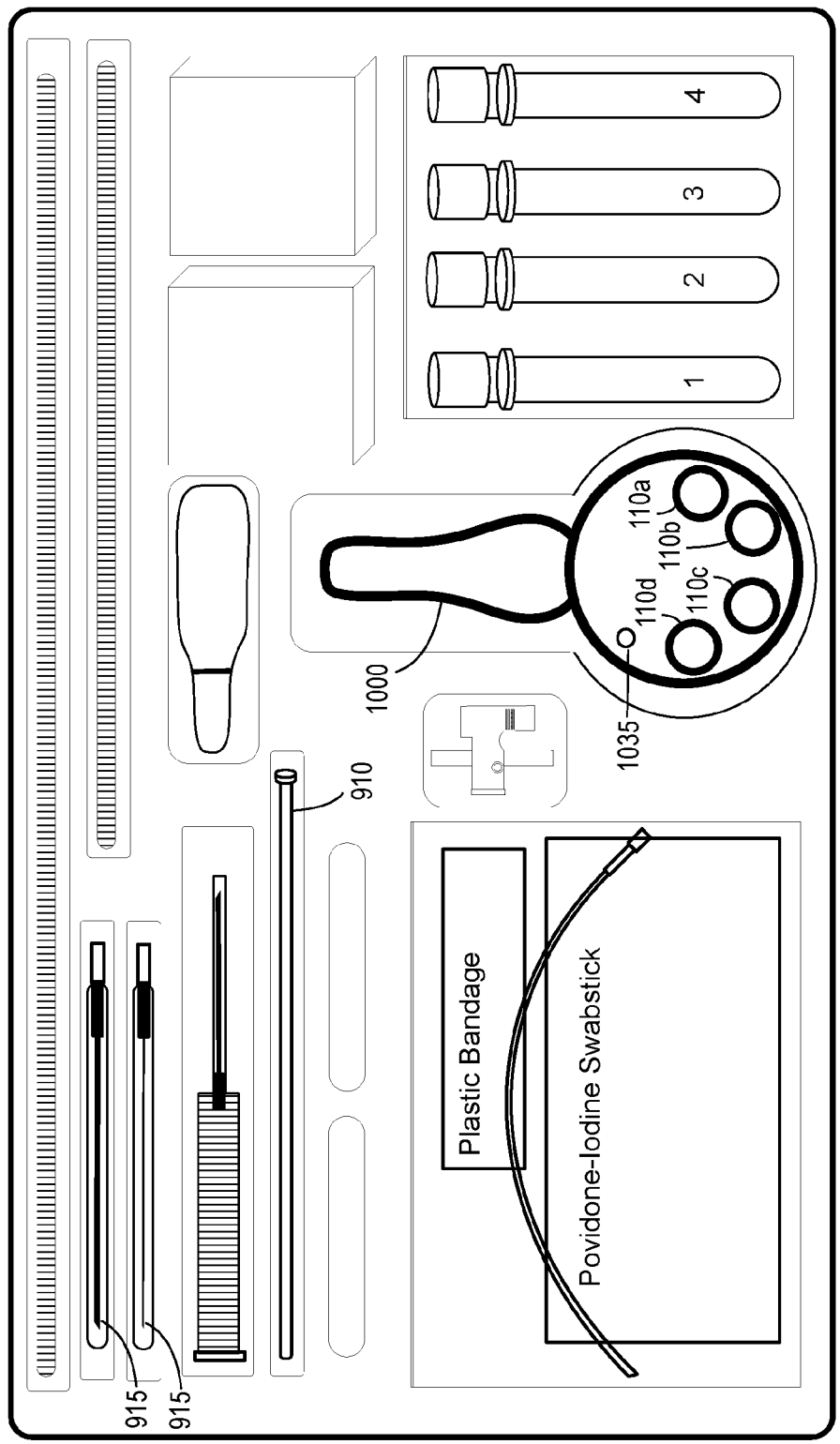
FIG. 12 is a diagram of a procedural tray according to one embodiment.

FIG. 12 is a diagram of a procedural tray according to one embodiment. The procedure tray includes a number of recesses that are adapted to hold a number of elements for a medical procedure, such as a lumbar puncture. For example, procedural tray includes a first recessed portion that is adapted to contain the vial and stylet holder 1000 or other vial and stylet holder described in this patent, and a second recessed portion that is adapted to contain the vials and caps. The procedural tray also includes a third recessed portion that is adapted to contain the stylet receptacle 910. The procedural tray also includes fourth and fifth recessed portion that are adapted to contain various size puncture needles 915.

While the procedural tray is shown as including a vial and stylet holder that is configured to hold four vials and four caps, the vial and stylet holder may be configured to hold more or fewer vials and caps. The procedural tray may be plastic and the recessed portions may be in the general shape of the objects being held. The procedural tray may include other items such as various syringes, medications, such as lidocaine, or other elements for a lumbar puncture. The procedural tray may also include instruction (not shown) regarding use of the tray's contents. The procedural tray may be packaged and then transferred to a lab providing for substantially minimal contact with the vials while sample are collected.

Figure 13:
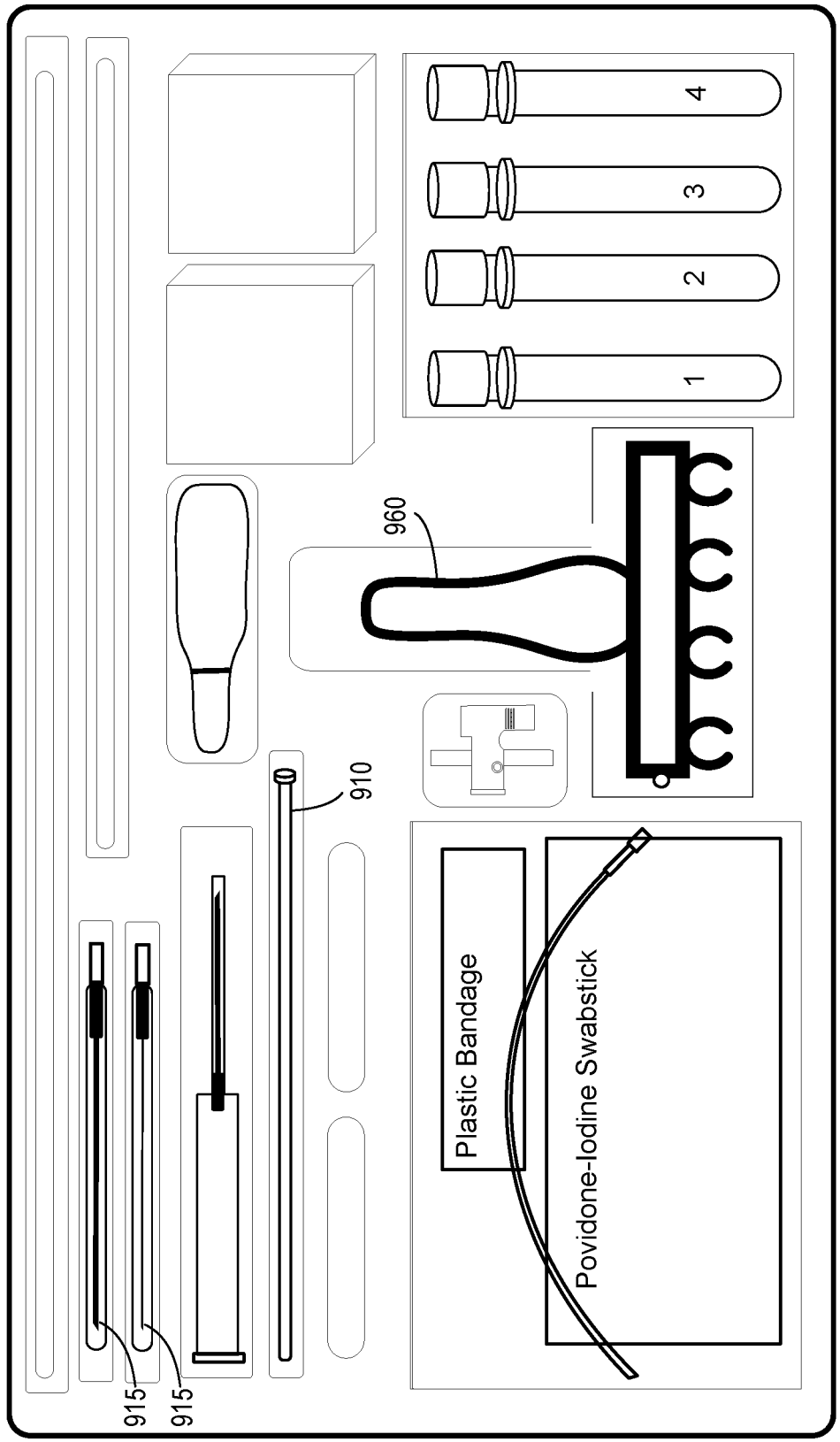
FIG. 13 is a diagram of a procedural tray according to another embodiment.

FIG. 13 is a diagram of a procedural tray according to another embodiment. The procedure tray is substantially similar to the procedural tray shown in FIG. 12 and as described above, but differs in that the procedural tray shown in FIG. 13 includes a recess adapted to contain the vial and stylet holder 960.

This description of the invention has been presented for the purposes of illustration and description. It is not intended to be exhaustive or to limit the invention to the precise form described, and many modifications and variations are possible in light of the teaching above. The implementations were chosen and described in order to best explain the principles of the invention and its practical applications. Various elements of the various embodiments described herein can be combined in some embodiments and not included in some embodiments. This description will enable others skilled in the art to best utilize and practice the invention in various implementations and with various modifications as are suited to a particular use. The scope of the invention is defined by the following claims.

The invention claimed is:

1. A vial and stylet holder comprising:
a vial frame;
a handle connected to the vial frame;
a plurality of vial holders coupled to an outer surface of the vial frame, wherein each of the vial holders includes a tube, each of the tubes has an opening formed in a side of the tube that extends from a first end of the tube to a second end of the tube, and each of the tubes is adapted to receive and hold a vial and to flex away from the opening of the tube when a vial is located in the vial holder to exert an inward force on a vial positioned in the tube and flex towards the opening of the tube when a vial is not located in the vial holder; and
a stylet receptacle coupled to the vial frame, wherein the stylet receptacle includes a tube having an opening at a first end of the tube, a longitudinal axis of the tube of the stylet receptacle is substantially parallel to longitudinal axes of each of the tubes of the vial holders, the stylet receptacle extends past a bottom of the vial frame, and the stylet receptacle is adapted to hold a stylet of a puncture needle.

2. The vial and stylet holder of claim 1, wherein the vial frame is a tube and the stylet receptacle is coupled to an outside surface of the tube of the vial frame.

3. The vial and stylet holder of claim 1, wherein the vial frame is a tube and the stylet receptacle is coupled to an inside surface of the tube of the vial frame.

4. The vial and stylet holder of claim 1, wherein the vial frame has a substantially quadrilateral shape and the stylet receptacle is coupled to an outside surface of the quadrilateral-shape vial frame.

5. The vial and stylet holder of claim 1, wherein the vial frame comprises a receptacle holder coupled to an outside surface of the tube of the vial frame, and the receptacle holder is adapted to removably receive the stylet receptacle.

6. The vial and stylet holder of claim 5, wherein the receptacle holder includes a tube having a top and a bottom that are open, and a diameter of the receptacle holder is greater than a diameter of the stylet receptacle.

7. The vial and stylet holder of claim 5, wherein the receptacle holder includes a rod having a channel that extends from a top of the rod to a bottom of the rod and the channel is tapered from the top of the rod to the bottom of the rod, and the channel has a side opening, a left sidewall, a right sidewall, and a back wall positioned between the left and right side openings, and an angle between the left and right sidewalls is greater than zero degrees.

8. The vial and stylet holder of claim 7, wherein the stylet receptacle includes a tab having a shape that substantially compliments the channel, and the channel is adapted to releasably receive the tab for coupling the stylet receptacle to the vial holder.

9. The vial and stylet holder of claim 1, wherein the vial frame is a disk having an aperture formed in the disk adapted to releasably-receive the stylet receptacle.

10. The vial and stylet holder of claim 1 comprising a plurality of cap holders connected to the vial frame, wherein each of the cap holders is positioned adjacent to one of the vial holders, each cap holder is adapted to hold a cap for capping a vial, each of the cap holders is configured to hold a cap above a top of a vial that is held by one of the vial apertures, and corresponding ones of the vial holders and the cap holders are positioned along common radiuses of the vial frame.

11. A vial and stylet holder comprising:
a vial frame having a rectangular shape;
a handle connected to the vial frame;
a plurality of vial holders coupled to an outer surface of the vial frame, wherein each of the vial holders includes a tube, each of the tubes has an opening formed in a side of the tube that extends from a first end of the tube to a second end of the tube, and each of the tubes is adapted to receive and hold a vial and to flex away from the opening of the tube when a vial is located in the vial holder to exert an inward force on a vial positioned in the tube and flex towards the opening of the tube when a vial is not located in the vial holder; and
a stylet receptacle aperture, having a tube shape, formed in the vial frame, wherein the stylet receptacle aperture extends from a top surface of the vial frame to a bottom surface of the vial frame, wherein a longitudinal axis of the stylet receptacle aperture is substantially parallel to longitudinal axes of each of the tubes of the vial holders, the stylet receptacle extends past a bottom of the vial frame, and the stylet receptacle is adapted to hold a stylet of a puncture needle.

12. The vial and stylet holder of claim 11, comprising a plurality of cap holders connected to the vial frame, wherein each of the cap holders is positioned adjacent to one of the vial holders, each cap holder is adapted to hold a cap for capping a vial, each of the cap holders is configured to hold a cap above a top of a vial that is held by one of the vial apertures, and corresponding ones of the vial holders and the cap holders are positioned along common radiuses of the vial frame.

13. A kit for a lumbar puncture comprising:
a procedure tray comprising a plurality of recesses;
a vial and stylet holder positioned in a first recess of the plurality of recesses, wherein the vial and stylet holder comprises:
a vial frame;
a handle connected to the vial frame;
a plurality of vial holders coupled to an outer surface of the vial frame, wherein each of the vial holders includes a tube, each of the tubes has an opening formed in a side of the tube that extends from a first end of the tube to a second end of the tube, and each of the tubes is adapted to receive and hold a vial and to flex away from the opening of the tube when a vial is located in the vial holder to exert an inward force on a vial positioned in the tube and flex towards the opening of the tube when a vial is not located in the vial holder; and
a receptacle holder, having a tube shape, coupled to the vial frame;
a stylet receptacle positioned in a second recess of the plurality of recesses, wherein the stylet receptacle includes a tube having an opening at a first end of the tube;
a puncture needle positioned in a third recess of the plurality of recesses, wherein the puncture needle comprises a stylet removably positioned in a central shaft of the puncture needle, the receptacle holder is adapted to removably receive the stylet receptacle and hold the stylet receptacle such that a longitudinal axis of the tube of the stylet receptacle is substantially parallel to longitudinal axes of each of the tubes of the vial holders, and the stylet receptacle extends past a bottom of the vial frame when the stylet receptacle is positioned in the receptacle holder; and
an instruction manual for using the kit.

14. The kit of claim 13 comprising a plurality of vials positioned in corresponding ones of the plurality of recesses.

15. The kit of claim 13, wherein the vial frame is a tube and the stylet receptacle is coupled to an outside surface of the tube of the vial frame.

16. The kit of claim 13, wherein the vial frame is a tube and the stylet receptacle is coupled to an inside surface of the tube of the vial frame.

17. The kit of claim 13, wherein the vial frame is rectangular and the stylet receptacle is coupled to an outside surface of the tube of the vial frame.

18. The kit of claim 13 comprising a plurality of cap holders connected to the vial frame, wherein each of the cap holders is positioned adjacent to one of the vial holders, each cap holder is adapted to hold a cap for capping a vial, each of the cap holders is configured to hold a cap above a top of a vial that is held by one of the vial apertures, and corresponding ones of the vial holders and the cap holders are positioned along common radiuses of the vial frame.

19. A vial and stylet holder comprising:
a vial frame having a rectangular shape;
a handle connected to the vial frame;
a plurality of vial holders formed in the vial frame, wherein each of the vial holders includes a tube shaped aperture formed in the vial frame, and each tube shaped apertures is adapted to receive a vial;
a stylet receptacle, having a tube shape, coupled to the vial frame, wherein the stylet receptacle has a longitudinal axis that is substantially parallel to longitudinal axes of each of the tube shaped apertures of the vial holders, the stylet receptacle extends past a bottom of the vial frame, and the stylet receptacle is adapted to hold a stylet of a puncture needle; and
a receptacle holder coupled to an outside surface of the vial frame, wherein the receptacle holder is adapted to removably receive the stylet receptacle.

* * * * *